US008188044B2

(12) United States Patent
Colin et al.

(10) Patent No.: US 8,188,044 B2
(45) Date of Patent: May 29, 2012

(54) ANTI-TUMOR DRUG, MEDICAMENT, COMPOSITION, AND USE THEREOF

(75) Inventors: Sylvie Colin, Paris (FR); Salman Al-Mahmood, Paris (FR)

(73) Assignee: Gene Signal International SA, Lausanne (CH)

( * ) Notice: Subject to any disclaimer, the term of this patent is extended or adjusted under 35 U.S.C. 154(b) by 401 days.

(21) Appl. No.: 12/608,507

(22) Filed: Oct. 29, 2009

(65) Prior Publication Data

US 2010/0047369 A1 Feb. 25, 2010

Related U.S. Application Data

(63) Continuation of application No. 11/783,654, filed on Apr. 11, 2007, now Pat. No. 7,674,770.

(51) Int. Cl.
*A61K 38/17* (2006.01)
*C07K 14/435* (2006.01)

(52) U.S. Cl. ..................... 514/13.3; 514/19.3; 514/21.2; 530/324

(58) Field of Classification Search ........................ None
See application file for complete search history.

(56) References Cited

U.S. PATENT DOCUMENTS 6,812,339 B1 11/2004 Venter et al.
7,674,770 B2 * 3/2010 Colin et al. .................... 514/1.1

* cited by examiner

*Primary Examiner* — Jeffrey E Russel
(74) *Attorney, Agent, or Firm* — Young & Thompson

(57) ABSTRACT

An active polypeptide comprising the amino acid sequence of SEQ ID NO: 3, or having at least 50%, preferably 70%, more preferably 90% identity with the amino acid sequence of SEQ ID NO: 3, or fragments thereof having at least 21 contiguous amino acids, or peptides having at least 50%, preferably 70%, more preferably 90% identity with the amino acid sequence of the fragments, provided that the polypeptide is not SEQ ID NO: 2. A method for inhibiting cancer and/or tumor growth comprising administering to a subject in need thereof an effective amount of the active polypeptide.

6 Claims, 7 Drawing Sheets

SEQUENCE LISTING

```
<160> NUMBER OF SEQ ID NOS: 15

<210> SEQ ID NO 1
<211> LENGTH: 1801
<212> TYPE: DNA
<213> ORGANISM: Homo sapiens

<400> SEQUENCE: 1

cttccccctc ccgcgcgccc gcccgccgcc tgccgccgcc gccgccgccg ccggagctct     60

gtagtatggc atcgaggaga atggagacca aacctgtgat aacctgtctc aaaaccctcc    120

tcatcatcta ctccttcgtc ttctggatca ctggggtgat cctgctggct gttggagtct    180

ggggcaaact tactctgggc acctatatct ccttattgc cgagaactcc acaaatgctc    240

cctatgtgct catcggaact ggcaccacta ttgttgtctt tggcctgttt ggatgctttg    300

ctacatgtcg tggtagccca tggatgctga aactgtatgc catgtttctg tccctggtgt    360

tcctggctga gctcgtagct ggcatttcag ggtttgtgtt tcgtcatgag atcaaggaca    420

ccttcctgag gacttacacg gacgctatgc agacttacaa tggcaatgat gagaggagcc    480

gggcagtgga ccatgtgcag cgcagcctga gctgctgtgg tgtgcagaac tacaccaact    540

ggagcaccag cccctacttc ctggagcatg gcatcccccc cagctgctgc atgaacgaaa    600

ctgattgtaa tccccaggat ctacacaatc tgactgtggc cgccaccaaa gttaaccaga    660

agggttgtta tgatctggta actagtttca tggagactaa catgggaatc atcgctggag    720

tggcgtttgg aatcgcattc tcccagttaa ttggcatgct gctggcctgc tgtctgtccc    780

ggttcatcac ggccaatcag tatgagatgg tgtaaggaga agtctttcaa gaatgacgga    840

ataagagacc tgttttaaaa aggaactgca gcaatctttg aaagacttcc aaagaatgtt    900

agagcacagt acataataca cttgccctgc tccctctccc ccttacccca caacgtgcaa    960

ctgacactcc cacccagtct ctgctccacc tttcagccca cgtcacgtgt agtgtccatt   1020

ttgtgaagcc ctgttgtgcc acagagtgta gccaggtccc cctgcagcta gtcctagtga   1080

acctcacccc gaggccctgc atgggccagc ccctccatct gtacttggtc caactgcaac   1140

tcatcatcgg tgactggtta tcacaccatc gctggcccct ttgggccctg catgtagtgt   1200
```

-continued

```
gggaggctcc tgttagctcc tcactgtggt aaatgccaca cacctttaag tagataagca   1260

gacgatagtt atctgttctt ttgacttaat ctcatttggt ttgattttcc ctctactaag   1320

gctttcctac cttcttcagg ctgcctaaga catgtaacga aacacttcaa taattgtcca   1380

tgaggagaaa aaaagcatgt gtcatgcatg aaggaaactg aacttgaggt ggcctccttg   1440

cttgttacat acctgggtat gtgtaggcag tttagtgcat ctttgcctct cggttgaaac   1500

ctgtataacc ctgttacaaa gctgtgttgt tgcttcttgt gaaggccatg atattttgtt   1560

tttccccaat taattgctat tgtgttattt tactacttct ctctgtattt tttcttgcat   1620

tgacattata gacattgagg acctcatcca aacaatttaa aaatgagtgt gaagggggaa   1680

caagtcaaaa tatttttaaa agatcttcaa aagtaatgcc tctgtctagc atgccaacaa   1740

gaatgcattg atattgtgaa catttgtgat atatgtatta ataaatagag caattacaag   1800

c                                                                    1801


<210> SEQ ID NO 2
<211> LENGTH: 244
<212> TYPE: PRT
<213> ORGANISM: Homo sapiens

<400> SEQUENCE: 2

Met Glu Thr Lys Pro Val Ile Thr Cys Leu Lys Thr Leu Leu Ile Ile
1               5                   10                  15

Tyr Ser Phe Val Phe Trp Ile Thr Gly Val Ile Leu Leu Ala Val Gly
            20                  25                  30

Val Trp Gly Lys Leu Thr Leu Gly Thr Tyr Ile Ser Leu Ile Ala Glu
        35                  40                  45

Asn Ser Thr Asn Ala Pro Tyr Val Leu Ile Gly Thr Gly Thr Thr Ile
    50                  55                  60

Val Val Phe Gly Leu Phe Gly Cys Phe Ala Thr Cys Arg Gly Ser Pro
65                  70                  75                  80

Trp Met Leu Lys Leu Tyr Ala Met Phe Leu Ser Leu Val Phe Leu Ala
                85                  90                  95

Glu Leu Val Ala Gly Ile Ser Gly Phe Val Phe Arg His Glu Ile Lys
            100                 105                 110

Asp Thr Phe Leu Arg Thr Tyr Thr Asp Ala Met Gln Thr Tyr Asn Gly
        115                 120                 125

Asn Asp Glu Arg Ser Arg Ala Val Asp His Val Gln Arg Ser Leu Ser
    130                 135                 140

Cys Cys Gly Val Gln Asn Tyr Thr Asn Trp Ser Thr Ser Pro Tyr Phe
145                 150                 155                 160

Leu Glu His Gly Ile Pro Pro Ser Cys Cys Met Asn Glu Thr Asp Cys
                165                 170                 175

Asn Pro Gln Asp Leu His Asn Leu Thr Val Ala Ala Thr Lys Val Asn
            180                 185                 190

Gln Lys Gly Cys Tyr Asp Leu Val Thr Ser Phe Met Glu Thr Asn Met
        195                 200                 205

Gly Ile Ile Ala Gly Val Ala Phe Gly Ile Ala Phe Ser Gln Leu Ile
    210                 215                 220

Gly Met Leu Leu Ala Cys Cys Leu Ser Arg Phe Ile Thr Ala Asn Gln
225                 230                 235                 240

Tyr Glu Met Val


<210> SEQ ID NO 3
<211> LENGTH: 112
```

<212> TYPE: PRT
<213> ORGANISM: Homo sapiens

<400> SEQUENCE: 3

```
Ile Ser Gly Phe Val Phe Arg His Glu Ile Lys Asp Thr Phe Leu Arg
1               5                   10                  15

Thr Tyr Thr Asp Ala Met Gln Thr Tyr Asn Gly Asn Asp Glu Arg Ser
            20                  25                  30

Arg Ala Val Asp His Val Gln Arg Ser Leu Ser Cys Cys Gly Val Gln
        35                  40                  45

Asn Tyr Thr Asn Trp Ser Thr Ser Pro Tyr Phe Leu Glu His Gly Ile
    50                  55                  60

Pro Pro Ser Cys Cys Met Asn Glu Thr Asp Cys Asn Pro Gln Asp Leu
65                  70                  75                  80

His Asn Leu Thr Val Ala Ala Thr Lys Val Asn Gln Lys Gly Cys Tyr
                85                  90                  95

Asp Leu Val Thr Ser Phe Met Glu Thr Asn Met Gly Ile Ile Ala Gly
            100                 105                 110
```

<210> SEQ ID NO 4
<211> LENGTH: 74
<212> TYPE: PRT
<213> ORGANISM: Homo sapiens

<400> SEQUENCE: 4

```
Gln Arg Ser Leu Ser Cys Cys Gly Val Gln Asn Tyr Thr Asn Trp Ser
1               5                   10                  15

Thr Ser Pro Tyr Phe Leu Glu His Gly Ile Pro Pro Ser Cys Cys Met
            20                  25                  30

Asn Glu Thr Asp Cys Asn Pro Gln Asp Leu His Asn Leu Thr Val Ala
        35                  40                  45

Ala Thr Lys Val Asn Gln Lys Gly Cys Tyr Asp Leu Val Thr Ser Phe
    50                  55                  60

Met Glu Thr Asn Met Gly Ile Ile Ala Gly
65                  70
```

<210> SEQ ID NO 5
<211> LENGTH: 49
<212> TYPE: PRT
<213> ORGANISM: Homo sapiens

<400> SEQUENCE: 5

```
Ile Pro Pro Ser Cys Cys Met Asn Glu Thr Asp Cys Asn Pro Gln Asp
1               5                   10                  15

Leu His Asn Leu Thr Val Ala Ala Thr Lys Val Asn Gln Lys Gly Cys
            20                  25                  30

Tyr Asp Leu Val Thr Ser Phe Met Glu Thr Asn Met Gly Ile Ile Ala
        35                  40                  45

Gly
```

<210> SEQ ID NO 6
<211> LENGTH: 43
<212> TYPE: PRT
<213> ORGANISM: Homo sapiens

<400> SEQUENCE: 6

```
Met Asn Glu Thr Asp Cys Asn Pro Gln Asp Leu His Asn Leu Thr Val
1               5                   10                  15

Ala Ala Thr Lys Val Asn Gln Lys Gly Cys Tyr Asp Leu Val Thr Ser
```

-continued 20 25 30

Phe Met Glu Thr Asn Met Gly Ile Ile Ala Gly
35 40

<210> SEQ ID NO 7
<211> LENGTH: 1051
<212> TYPE: DNA
<213> ORGANISM: Homo sapiens
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (832)..(832)
<223> OTHER INFORMATION: n is a, c, g, or t
<220> FEATURE:
<221> NAME/KEY: misc_feature
<222> LOCATION: (841)..(841)
<223> OTHER INFORMATION: n is a, c, g, or t
<220> FEATURE:
<221> NAME/KEY: misc_feature
<222> LOCATION: (858)..(858)
<223> OTHER INFORMATION: n is a, c, g, or t
<220> FEATURE:
<221> NAME/KEY: misc_feature
<222> LOCATION: (862)..(862)
<223> OTHER INFORMATION: n is a, c, g, or t
<220> FEATURE:
<221> NAME/KEY: misc_feature
<222> LOCATION: (869)..(869)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (910)..(910)
<223> OTHER INFORMATION: n is a, c, g, or t
<220> FEATURE:
<221> NAME/KEY: misc_feature
<222> LOCATION: (918)..(918)
<223> OTHER INFORMATION: n is a, c, g, or t
<220> FEATURE:
<221> NAME/KEY: misc_feature
<222> LOCATION: (922)..(922)
<223> OTHER INFORMATION: n is a, c, g, or t
<220> FEATURE:
<221> NAME/KEY: misc_feature
<222> LOCATION: (942)..(942)
<223> OTHER INFORMATION: n is a, c, g, or t
<220> FEATURE:
<221> NAME/KEY: misc_feature
<222> LOCATION: (965)..(965)
<223> OTHER INFORMATION: n is a, c, g, or t
<220> FEATURE:
<221> NAME/KEY: misc_feature
<222> LOCATION: (991)..(991)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1015)..(1015)
<223> OTHER INFORMATION: n is a, c, g, or t
<220> FEATURE:
<221> NAME/KEY: misc_feature
<222> LOCATION: (1042)..(1042)
<223> OTHER INFORMATION: n is a, c, g, or t
<220> FEATURE:
<221> NAME/KEY: misc_feature
<222> LOCATION: (1048)..(1048)
<223> OTHER INFORMATION: n is a, c, g, or t

<400> SEQUENCE: 7

```
tgtgagcgga tacattcccc tctagaaata attttgttta actttaagaa ggagatatnc     60

atatgcacca tcatcatcat cattcttctg gtctggtgcc acgcggttct ggtatgaaag    120

aaaccgctgc tgctaaattc gaacgccagc acatggacag cccagatctg ggtaccgatg    180

acgacgacaa gatttcaggg tttgtgtttc gtcatgagat caaggacacc ttcctgagga    240

cttacacgga cgctatgcag acttacaatg gcaatgatga gaggagccgg gcagtggacc    300

atgtgcagcg cagcctgagc tgctgtggtg tgcagaacta caccaactgg agcaccagcc    360

cctacttcct ggagcatggc atcccccccca gctgctgcat gaacgaaact gattgtaatc    420

cccaggatct acacaatctg actgtggccg ccaccaaagt taaccagaag ggttgttatg    480

atctggtaac tagtttcatg gagactaaca tgggaatcat cgctggagac cgggcttctc    540

ctcaaccatg gcgatatcgg atccgaattc tagctccgtc gacaagcttg cggccgcact    600

cgagcaccac caccaccacc actgagatcc ggctgctaac aaagcccgaa aggaagctga    660

gttggctgct gccaccgctg agcaataact agcataaccc cntggggcct ctaaacgggt    720

cttgaggggt tttttgctga aaggaggaac tatatccgga ttggcgaatg ggacgcgccc    780

tgtagcggcg cataaagcgc ggcgggtgtg gtggttacgc gcagcgtgac gnctaacttg    840

ncagcgccct agcgcccnct cntttcgcnt ttcttccctt cctttctcgc ncgtttcgcc    900

ggctttcccn gtcagctnta antcgggggg ctcccttagg gntccattta gtgctttacg    960

gcccncaccc caaaaacttg attaaggtga ngggttcccg aatgggcntc ccccntgata   1020

acggttttc ccctttgacg tngagtcnct t                                   1051
```

<210> SEQ ID NO 8
<211> LENGTH: 209
<212> TYPE: PRT
<213> ORGANISM: Homo sapiens
<220> FEATURE:
<221> NAME/KEY: misc_feature
<222> LOCATION: (188)..(188)
<223> OTHER INFORMATION: Xaa can be any naturally occurring amino acid

<400> SEQUENCE: 8

```
Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Asp Lys Ile Ser Gly Phe Val
        35                  40                  45

Phe Arg His Glu Ile Lys Asp Thr Phe Leu Arg Thr Tyr Thr Asp Ala
    50                  55                  60

Met Gln Thr Tyr Asn Gly Asn Asp Glu Arg Ser Arg Ala Val Asp His
65                  70                  75                  80

Val Gln Arg Ser Leu Ser Cys Cys Gly Val Gln Asn Tyr Thr Asn Trp
                85                  90                  95

Ser Thr Ser Pro Tyr Phe Leu Glu His Gly Ile Pro Pro Ser Cys Cys
            100                 105                 110

Met Asn Glu Thr Asp Cys Asn Pro Gln Asp Leu His Asn Leu Thr Val
        115                 120                 125

Ala Ala Thr Lys Val Asn Gln Lys Gly Cys Tyr Asp Leu Val Thr Ser
    130                 135                 140
```

-continued

```
Phe Met Glu Thr Asn Met Gly Ile Ile Ala Gly Asp Arg Ala Ser Pro
145                 150                 155                 160

Gln Pro Trp Arg Tyr Arg Ile Arg Ile Leu Ala Pro Ser Thr Ser Leu
                165                 170                 175

Arg Pro His Ser Ser Thr Thr Thr Thr Thr Thr Xaa Ile Arg Leu Leu
            180                 185                 190

Thr Lys Pro Glu Arg Lys Leu Ser Trp Leu Leu Pro Pro Leu Ser Asn
        195                 200                 205

Asn


<210> SEQ ID NO 9
<211> LENGTH: 44
<212> TYPE: DNA
<213> ORGANISM: Homo sapiens

<400> SEQUENCE: 9

gacgacgaca agatttcagg gtttgtgttt cgtcatgaga tcaa                      44


<210> SEQ ID NO 10
<211> LENGTH: 37
<212> TYPE: DNA
<213> ORGANISM: Homo sapiens

<400> SEQUENCE: 10

gaggagaagc ccggtctcca gcgatgattc ccatgtt                              37


<210> SEQ ID NO 11
<211> LENGTH: 33
<212> TYPE: DNA
<213> ORGANISM: Homo sapiens

<400> SEQUENCE: 11

gacgacgaca agatgcagcg cagcctgagc tgc                                  33


<210> SEQ ID NO 12
<211> LENGTH: 33
<212> TYPE: DNA
<213> ORGANISM: Homo sapiens

<400> SEQUENCE: 12

gacgacgaca agatccccc cagctgctgc atg                                  33


<210> SEQ ID NO 13
<211> LENGTH: 37
<212> TYPE: DNA
<213> ORGANISM: Homo sapiens

<400> SEQUENCE: 13

gacgacgaca agatgaacga aactgattgt aatcccc                              37


<210> SEQ ID NO 14
<211> LENGTH: 30
<212> TYPE: DNA
<213> ORGANISM: Homo sapiens

<400> SEQUENCE: 14

gacgacgaca agatggaccg ggcttctcct                                      30


<210> SEQ ID NO 15
<211> LENGTH: 33
<212> TYPE: DNA
<213> ORGANISM: Homo sapiens
```

-continued

<400> SEQUENCE: 15
gaggagaagc ccggtctagt tattgctcag cgg 33

ANTI-TUMOR DRUG, MEDICAMENT, COMPOSITION, AND USE THEREOF

CROSS REFERENCE TO RELATED APPLICATION

This application is a continuation of application Ser. No. 11/783,654 filed on Apr. 11, 2007. The entire contents of the above-identified application are hereby incorporated by reference.

The present invention relates to the field of treatments for cancers. More specifically, the present invention relates to the treatment of cancers by polypeptides derived from a protein belonging to the tetraspanin super family.

Cancer is a class of diseases or disorders characterized by uncontrolled division of cells and the ability of these cells to spread, either by direct growth into adjacent tissue through invasion, or by implantation into distant sites by metastasis (where cancer cells are transported through the bloodstream or lymphatic system). Cancer may affect people at all ages, but risk tends to increase with age. It is one of the principal causes of death in developed countries.

There are many types of cancer. Severity of symptoms depends on the site and character of the malignancy and whether there is metastasis. Once diagnosed, cancer is usually treated with a combination of surgery, chemotherapy and radiotherapy. As research develops, treatments are becoming more specific for the type of cancer pathology. Drugs that target specific cancers already exist for several cancers. If untreated, cancers may eventually cause illness and death, though this is not always the case.

Current treatments target distinct properties of malignant cells, such as for example evading apoptosis, unlimited growth potential (immortalization) due to overabundance of telomerase, self-sufficiency of growth factors, insensitivity to anti-growth factors, increased cell division rate, altered ability to differentiate, no ability for contact inhibition, ability to invade neighbouring tissues, ability to build metastases at distant sites, ability to promote blood vessel growth (angiogenesis).

Tumor angiogenesis is the proliferation of a network of blood vessels that penetrates into the tumor, supplying nutrients and oxygen and removing waste products. Tumor angiogenesis actually starts with cancerous tumor cells releasing molecules that send signals to surrounding normal host tissue. This signalling activates certain genes in the host tissue that, in turn, make proteins to encourage growth of new blood vessels. Solid tumors must stimulate the formation of new blood vessels in order to obtain the nutrients and oxygen necessary for their growth, thus providing a route by which the tumors can metastasize to distant sites.

Experimental evidence has suggested that malignant tumors can induce angiogenesis through the elaboration of a variety of factors, such as acidic fibroblast growth factor (aFGF), basic fibroblast growth factor (bFGF), vascular endothelial growth factor (VEGF), platelet derived growth factor (PDGF), transforming growth factor alpha (TGF-alpha), tumor necrosis growth factor alpha (TNF-alpha), and many others (Liotta et al., 1991, *Cell* 64: 327-336; Hanahan et al., *Cell* 86: 353-364).

Nowadays, plenty of chemotherapeutic molecules targeting angiogenesis are available on the market. Well known naturally occurring angiogenesis inhibitors are angiostatin, endostatin, interferons, platelet factor 4, prolactin 16 Kd fragment, thrombospondin, TIMP-1 (tissue inhibitor of metalloprotease-1), TIMP-2 and TIMP-3. These molecules can be used as chemotherapeutic treatments, as well as other drugs such as for example combrestatin A4, EMD 121974, TNP-470, squalamine, thalidomide, interferon-alpha, anti-VEGF, antibodies . . . . However, their efficiency is never sufficient and alternative treatments are desirable.

There is therefore a need of alternative chemotherapeutic agents for the treatment of tumors, having increased efficiency, being less invasive or toxic, and resulting in an increased rate of recovery.

WO 03/074073, in the name of the Applicant, describes a family of 54 genes involved in the regulation of angiogenesis. Amongst these genes, "gene 497" (SEQ ID No 1 in this specification), which encodes "protein 497" (SEQ ID No 2 in this specification), also called TM4SF2 in WO 03/074073, has been described as implied in the activation of angiogenesis (pro-angiogenic). The expression of gene 497 is enhanced when angiogenesis is stimulated by pro-angiogenic factors such as VEGF and FGF2. WO 03/074073 also describes that the expression of an antisens of the gene 497, i.e. the inhibition of the expression of the gene 497, in human endothelial cells inhibits the formation of capillary tubes.

Bio-informatics analysis revealed that protein 497C, which comprises 244 amino-acids, contains one extracellular loop SEL (Small Extracellular Loop), one extracellular loop LEL (Large Extracellular Loop), four trans-membrane spans and two intracellular tails corresponding to the N- and C-terminals. Thus, this protein has been classified as a member of the tetraspanin super family (Levy et al., *Nat Rev Immunol.* 2005 February; 5(2):136-48).

The tetraspanins are a large family of evolutionarily conserved cell-surface proteins that are expressed in a wide range of organisms. Members of this family tend to associate with each other, together with their partners, in membrane microdomains that provide a scaffold for the transmission of external stimuli to intracellular-signalling components. Basically, tetraspanins comprise four transmembrane (TM) domains which contain conserved polar residues and flank the small and large extracellular loops (SEL and LEL respectively). The LEL is composed of a core formed by helices a, b and e, and this core structure is conserved among the tetraspanins. Helices c and d comprise the variable portion of the LEL, and they are flanked by the CCG motif and further conserved cysteine residues. This region is folded as a result of disulphide bridges to form a mushroom-like structure.

The members of this super-family have been classified into three groups based on the number of cysteine residues present in the LEL domain. Group 1 contains four cysteines in the LEL domain, group 2 contains six cysteines in the LEL domain, and group 3 contains eight cysteines in the LEL domain.

Since protein 497C contains six cysteines within its LEL domain, it could therefore be classified in group 2, similarly to protein CD151, another member of this family. The LEL domain of these proteins comprises 6 domains: a, b, c, d1, d2 and e, among which d1, d2 and c consist in the variable portions of the LEL.

Going deeper in their researches, the inventors produced truncated forms of protein 497C, corresponding to the various fragments of the extracellular domain SEL and LEL of protein 497C:

- 497C-T2: entire LEL domain of protein 497C, identified by SEQ ID NO:3 in this specification (112 amino acids),
- 497C-T3: c, d1, d2 and e domains of the LEL domain, identified by SEQ ID NO:4 in this specification (74 amino acids),
- 497C-T4: d1, d2 and e domains of the LEL domain, identified by SEQ ID NO:5 in this specification (49 amino acids), 497C-T5: d2 and e domains of the LEL domain, identified by SEQ ID NO:6 in this specification (43 amino acids).

To ensure the three-dimensional configuration of these fragments, i.e. the three-dimensional conformation of the LEL domain, and therefore their potential activity inventors added, according to an embodiment, a tail at the C-terminus of the fragments. This tail was composed of a random sequence of 30 to 70 amino acids, preferably of 45 to 65 amino acids, more preferably of 50 to 60 amino acids, still more preferably of about 55 amino acids. This tail has no activity per se, and its presumed role is to stabilize the three-dimensional structure of the LEL fragment, i.e. to maintain the polypeptide folded in a biologically active form.

In a first experiment, the inventors found that protein 497C-T2 may inhibit human endothelial cell proliferation in vitro in a dose dependent manner.

Then, in a second experiment, the inventors surprisingly found that the truncated forms of protein 497C may have a strong activity to inhibit capillary tube formation in vitro, in a dose dependent manner.

Other experiments conducted by the inventors suggested that truncated forms of protein 497C induced the inhibition of the migration of endothelial cells in vitro, in a dose dependent manner. The results of the dose-response study on the inhibition of angiogenesis by 497C-T2 revealed that at 270 nM, the recombinant protein 497C-T2 induced a small inhibition while at 540 nM, 497C-T2 may inhibit by more than 50% in vitro angiogenesis (i.e. $IC_{50}$<540 nM). This demonstrated that the recombinant protein 497C-T2 is a potent anti-angiogenic compound, and that it could be at least 200-fold more potent than the anti-VEGF mAb and/or VEGF receptor (KDR)-based identified peptides (Binetruy-Tournaire R et al., Identification of a peptide blocking vascular endothelial growth factor (VEGF)-mediated angiogenesis, *EMBO J.* 2000; 19: 1525-1533).

Capillary tube formation, human endothelial cell proliferation and human endothelial cell migration are three essential steps of angiogenesis. Consequently, the fact that 497C-T2 may inhibit in vitro capillary tube formation, human endothelial cell proliferation and/or migration in a dose-dependant manner, thus constituted a strong evidence of the potent anti-angiogenic activity of the truncated forms of protein 497C.

All these results were absolutely unexpected since native protein 497C has been disclosed as pro-angiogenic and that the expression of an antisens of the gene 497, i.e. the inhibition of gene 497, in human endothelial cells inhibits the formation of capillary tubes. It was therefore really surprising that truncated forms of protein 497C, may have anti-angiogenic activity.

In addition, inventors tested the effect of 497C-T2 on the proliferation of many cell lines, including the fibroblast cell line MRC5, CHO, the tumor cell lines Calu-6, NCI-H460, and more, without any detectable anti-proliferative effect even at high concentration. In contrast, 497C-T2 significantly inhibited human endothelial cell proliferation for concentration as low as 500 nM, reaching 75% inhibition at 5 μM. Hence, in addition of being more potent than the anti-VEGF therapeutic strategies available today, 497C-T2 is highly specific to endothelial cells.

Interestingly, the inventors found that the truncated form 497C-T3, which lack the a and b domains, was almost as potent than 497C-T2 on the inhibition of angiogenesis and cell migration, indicating that the a and b domains only slightly contribute to the biological activity and/or to the three dimensional conformation necessary for the biological activity of 497C-T2. The truncated forms 497C-T4 (lacking the a, b, and c domains), and 497C-T5 (lacking the a, b, c, and d1 domains) had limited activities relative to that of 497C-T2, indicating that both the c and d1 domains are necessary for the activity of the protein 497C-T2.

These results were also unexpected, and led the inventors to test the anti-tumor activity of 497C-T2 in mice in vivo.

Still surprisingly, the inventors found that protein 497C-T2 had a strong anti-tumor activity in vivo, and a strong synergistic activity in combination with other chemotherapeutic agent such as for example cisplatin.

Inventors found that the test substance 497C-T2 was not toxic in Nude mice bearing human NCI H460 or CALU-6 tumors at different tested doses. Moreover, 497C-T2 exhibited a strong statistically significant anti-tumoral activity against NCI H460 and CALU-6 tumors as early as two days after the beginning of the treatment ($2^{nd}$ IP injection combined with CDDP). This anti-tumoral activity was persistent during the treatment period. The anti-tumoral effect of 497C-T2 in this model of human lung cancer represented a realistic therapeutic approach as a monotherapy. Its efficacy was strongly potentiated when combined with the cytotoxic anti-cancer drug CDDP (Cisplatin), which suppressed tumor growth. Cisplatin alone, on the other hand, did not eradicate tumor growth.

It is not clear whether the anti-angiogenic activity of 497C-T2 is solely responsible for its anti-tumoral activity. It is now accepted that biological compounds such as interferon, EGF and Her-2 receptor antagonists can modulate host responses and enhance the efficacy of standard chemotherapies. The data strongly suggested that 497C-T2 may be of use either as a primary anti-tumoral agent or as an add-on synergic therapy to primary cytotoxic agents for the treatment of cancers.

As mentioned above, it is now established that protein 497C is expressed in endothelial cells, and that its expression is enhanced when angiogenesis is stimulated by pro-angiogenic factors such as VEGF and FGF2 (see WO 2003/074073). Protein 497C belongs to the Tetraspanins superfamily, which are transmembrane receptors comprising two extracellular loops, implied in the recognition of extracellular signals, and two intracellular tails (C-terminal and N-terminal), implied in the transduction of the signal. A key feature in the signal transduction is the formation of a ligand-receptor complex between the extracellular loop of the receptor and the ligand. Without wanting to be bound with a theory, Applicants think that the truncated forms of 497C may play their role through a "soluble receptor mechanism": truncated forms of 497C may remain soluble on the surface of the cell and may be recognized by the ligand. As a result, there may be a competition in the recognition of the ligand between the soluble forms of 497C (the fragments of the invention) and the native transmembrane protein, and consequently a decrease, in a dose dependent manner, of the transduction of the pro-angiogenic signal, therefore resulting in the inhibition of angiogenesis and then in the decrease of tumour volume.

The present invention thus relates, in a first aspect, to an active polypeptide comprising the amino acid sequence of SEQ ID NO:3, or having at least 50%, preferably 70%, more preferably 90% identity with the amino acid sequence of SEQ ID NO:3, or fragments thereof having at least 21 contiguous amino acids, or peptides having at least 50%, preferably 70%, more preferably 90% identity with the amino acid sequence of said fragments, provided that said polypeptide is not SEQ ID NO:2.

As used herein, "peptide" means short molecules formed from the linking, in a defined order, of less than 100 amino acids.

As used herein, "polypeptide" means molecules formed from the linking, in a defined order, of at least 100 amino acids.

As used herein, "active polypeptide" means polypeptides which have a biological activity. In the present invention the polypeptides have an anti angiogenic and anti tumour activity.

In an embodiment, the polypeptides according to the invention further comprise means for having it folded in an active three dimensional conformation. Preferably, said means for having it folded in an active conformation consists in any sequence comprising from 30 to 70 amino acids, preferably from 45 to 65 amino acids, more preferably from 50 to 60 amino acids, still more preferably of about 55 amino acids, said sequence being fused to the C-terminus of said polypeptide.

As used herein, "three dimensional conformation" means the tertiary structure of a polypeptide, i.e. its overall shape, in which the polypeptide performs a biological function.

As used herein, the term "fragments" means truncated forms of the LEL domain of protein 497C, having an anti-tumor activity. Said fragments preferably have an amino acid sequence of at least 21 contiguous amino acids of SEQ ID NO:3. In a particular embodiment, the fragments have an amino acid sequence of at least 43 contiguous amino acids. In another particular embodiment, said fragments have the amino acid sequence of SEQ ID N:4 (74 amino acids), SEQ ID N:5 (49 amino acids) or SEQ ID N:6 (43 amino acids). Fragments also include peptides having at least 50%, preferably 70%, more preferably 90% identity with the amino acid sequence of said fragments, and having an anti-tumor activity.

In a second aspect, the present invention relates to a medicament comprising a polypeptide, a fragment, and/or a peptide as described above.

In a third aspect, the present invention relates to a pharmaceutical composition comprising a polypeptide, a fragment, and/or a peptide as described above, and one or more pharmaceutically-acceptable excipients.

In a fourth aspect, the invention relates to a pharmaceutical composition comprising a polypeptide, a fragment, and/or a peptide as described above, and one or more pharmaceutically-acceptable excipients, for use in a method of treatment of cancer and/or tumors of the human or animal body.

In a particular embodiment, the pharmaceutical compositions as described above further comprise at least one other active substance selected from anti-angiogenic substances or anti-tumor substances. These substances may be chosen by the man in the art, regarding the effect to be achieved. Preferably, these substances can be selected from cisplatin, carboplatin, etoposide, ifosfamide, mitomycin, vinblastine, vinorelbine, gemcitabine, paclitaxel, docetaxel, and irinotecan, etc. . . . .

In a fifth aspect, the invention relates to a pharmaceutical composition comprising synergistic effective amounts of

- a polypeptide, a fragment, and/or a peptide as described above, and
- a platinum complex selected from the group consisting of cisplatin and carboplatin.

The medicament or composition useful in the practice of this invention is administered to the mammal by known conventional routes. The medicament or composition described herein may be administered by the same route, or by different routes. For example, the medicament or composition may be administered to patients orally or parenterally (intravenously, subcutaneously, intramuscularly, intraspinally, intraperitoneally, and the like).

When administered parenterally, the composition is preferably formulated in a unit dosage injectable form (solution, suspension, emulsion) with at least one pharmaceutically acceptable excipient. Such excipients are typically nontoxic and non-therapeutic. Examples of such excipients are water, aqueous vehicles such as saline, Ringer's solution, dextrose solution, and Hank's solution and non-aqueous vehicles such as fixed oils (e.g., corn, cottonseed, peanut and sesame), ethyl oleate, and isopropyl myristate. Sterile saline is a preferred excipient. The excipient may contain minor amounts of additives such as substances that enhance solubility, isotonicity, and chemical stability, e.g., antioxidants, buffers, and preservatives. When administered orally (or rectally) the compounds will usually be formulated into a unit dosage form such as a table, capsule, suppository, or cachet. Such formulations typically include a solid, semi-solid or liquid carrier or diluent. Exemplary diluents and excipients are lactose, dextrose, sucrose, sorbitol, mannitol, starches, gum acacia, calcium phosphate, mineral oil, cocoa butter, oil of *theobroma*, alginates, tragacanth, gelatin, methylcellulose, polyoxyethylene, sorbitan monolaurate, methyl hydroxybenzoate, propyl hydroxybenzoate, talc and magnesium stearate. In preferred embodiments, the pharmaceutical composition according to the invention is administered intravenously.

According to the invention, the amount of polypeptide present in the medicament or composition is effective to treat susceptible tumors. Preferably, the polypeptide is present in an amount from 0.01 to 90% in weight, preferably from 0.1% to 10% in weight, more preferably from 1% to 5% in weight, in the medicament or in the composition. These amounts are routinely adaptable by the man in the art, who is able to choose the best quantity to administer to a patient to achieve recovery.

In a sixth aspect, the invention relates to the use of the polypeptide, fragment, and/or of the peptide as described above, or of the medicament as described above, or of the pharmaceutical composition as described above, for the treatment of cancers and/or tumors.

According to the invention, the tumors to be treated are preferably solid tumors. More preferably, the tumors to be treated are selected from sarcomas, carcinomas, and lymphomas. Examples of such tumors are bladder cancer, melanoma, breast cancer, non-Hodgkin's lymphoma, brain cancer, bone cancer, colon and rectal cancer, liver cancer, pancreatic cancer, endometrial cancer, prostate cancer, kidney cancer, skin cancer (non-melanoma), thyroid cancer, lung cancer (small cell lung cancer and non small cell lung cancer).

In a seventh aspect, the present invention relates to a method of treatment comprising administering to a subject in need of treatment the polypeptide, fragment, and/or the peptide as described above, or the medicament as described above, or the pharmaceutical composition as described above, in an amount sufficient to inhibit cancer or tumor growth.

In a particular embodiment, the invention relates to the method of treatment as described above further comprising administering at least one other anti-neoplastic or anti-tumor drug.

In these methods, administering comprises topical administration, oral administration, intravenous administration, or intraperitoneal administration.

In an eight aspect, the present invention relates to a method of treatment comprising administering to a subject in need of treatment a synergistic effective amount of

- a polypeptide, a fragment, and/or a peptide as described above, and
- a platinum complex selected from the group consisting of cisplatin and carboplatin, which is sufficient to inhibit cancer or tumor growth.

In one embodiment, said polypeptide or fragments thereof and said platinum complex are administered simultaneously.

In another embodiment, said polypeptide or fragments thereof and said platinum complex are administered sequentially. Preferably, said polypeptide or fragments thereof and said platinum complex are administered by separate routes, i.e. orally or parenterally (intravenously, subcutaneously, intramuscularly, intraspinally, intraperitoneally, and the like).

In a particular embodiment, said platinum complex is cisplatin.

In another particular embodiment said platinum complex is carboplatin.

The present invention will now be further described with reference to the following non-limiting examples.

FIG. 1 is a diagram representing the % inhibition of endothelial cell proliferation in vitro with increasing concentrations of protein 497C-T2.

FIGS. 2*a*, 2*b*, 2*c*, 2*d*, 2*f*, 2*g*, 2*h* and 2*i* are pictures of in vitro angiogenesis of endothelial cells in different conditions:

FIG. 2*a*: Control (Buffer Urea 2M)

FIG. 2*i*: C-terminal tail 53 μg/mL (4.14 μM)

FIGS. 3*a*, 3*b*, 3*c*, 3*d*, 3*e*, 3*f*, 3*g* are pictures of wound assay on endothelial cells performed in different conditions:

FIG. 3*g*: C-terminal tail 63 μg/mL (4.92 μM)

EXAMPLE 1

Production of Protein 497C-T2

Figure 1:
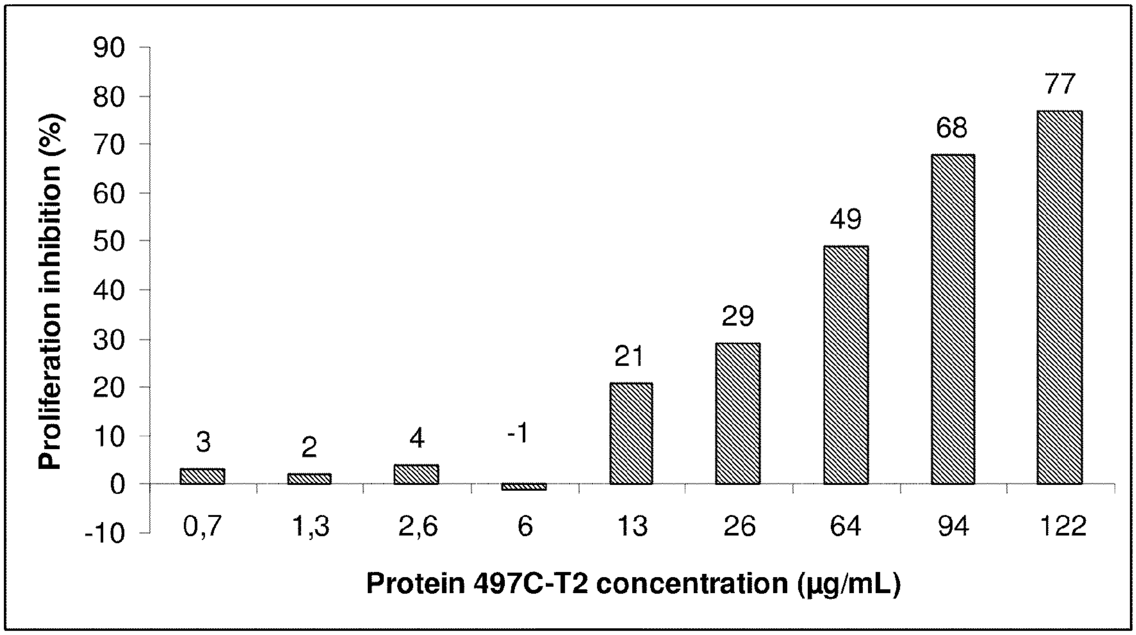

Synthesis of Insert 497C-T2:

First, gene 497C was cloned in pGEM®-T easy vector system (Promega®) according to known procedures (the vector obtained was called "pGEM-T-497C").

Second, the insert T2 (SEQ ID NO:3) corresponding to the extra-cellular part LEL of the protein 497C was amplified by PCR using the plasmid "pGEM-T-497C" and the two primers CDS5 and CDS4 (table 1), which frame the LEL domain in 5' and 3', respectively.

TABLE 1

| Primer | SEQ ID NO | Sequence |
|---|---|---|
| 497c-cds-5 | 9 | GACGACGACAAGATttcagggtttgtgtttcgtcatgagatcaa |
| 497c-cds-4 | 10 | <u>GAGGAGAAGCCCGGT</u>ctccacccatcattcccatctt |

Third, the DNA sequence coding for the protein 497C-T2 was inserted into the vector pET-30 EK/LIC (Novagen®) according to known procedures (pET-30-497C-T2). The nucleic acid sequence coding for 497C-T2 within the pET-30 vector is given in SEQ ID NO:7.

The purified vector was then introduced in *E. coli* BL21 (DE3) pLys for protein production. Colonies were controlled for the presence of both the vector end the insert by PCR.

The size of the produced protein 497C-T2 was 24 kD, and it was higher than the expected size. This was due to the addition of a supplementary tail at the C-terminal (54 random amino acids) as well as of a His-Tag at the N-terminal as confirmed by sequencing. The amino acid sequence of the protein 497C-T2 as produced is given in SEQ ID NO:8. The protein 497C-T2 was produced within the insoluble fraction of the bacteria, which necessitated an extraction in denaturating conditions.

Extraction and Purification of the Protein 497C-T2

Following culture, bacteria were lyzed, centrifuged and the supernatant discarded. The insoluble fraction obtained was treated with Tris-HCl 20 mM, urea 8 M, imidazol 5 mM, NaCl 0.5 M, GSH 5 mM, pH 8.0. After this treatment, the suspension was centrifuged and the supernatant collected, filtered on 0.45 μm membranes to discard insoluble materials. The filtered extract was then used to purify the protein 497C-T2 by using a His-Trap column (Amersham®) connected to a HPLC system (Amersham).

The purified protein obtained was diluted in 4 M urea and 0.3 M imidazol. To remove these agents from the preparation, the solution was subjected to dialysis at 4° C.

Following these steps of dialysis, the purified protein was centrifuged at 4,000×g for 15 min and filtered on 0.45 μm membranes to eliminate possible precipitates. The purified protein preparation was controlled for protein content according to the method described by Bradford in 1976 (Anal. Biochem. 72:248-54) and by SDS-PAGE. The gels were analyzed using the Gene Genius software to quantify the purity by image analysis.

To increase purity of the protein 497C-T2, we performed a second purification step by using ion exchange liquid chromatography. The HisTrap purified preparation was diluted 3 times with the buffer Tris-HCl 20 mM, pH 8, 2 M urea (to decrease the concentration of NaCl to 50 mM), and loaded on MonoS column connected to a HPLC system run by Unicorn software (Amersham, GE, Saclay, France). The column was then washed extensively and eluted with a linear gradient of ionic force (0.05 M to 0.5 M NaCl in the Tris-HCl 20 mM buffer, pH 8, 2 M urea). The purified protein preparation was controlled for protein content both by Bradford and by SDS-PAGE.

EXAMPLE 2

Design and Production of the Truncated Forms 497C-T3, 497C-T4, and 497C-T5

To identify the active site of the protein 497C-T2, three others truncated forms called 497C-T3, 497C-T4, and 497C-T5 were designed and produced as well as a control polypeptide corresponding to both the N-terminal attached His-Tag and the C-terminal tail coming from the vector. To do so, 5' specific primers were designed allowing the progressive truncation of the N-terminal sequence of the protein 497C-T2 without affecting the N-terminal His-Tag necessary for the purification of the produced truncated forms.

497C-T3

The truncated 497C-T3 was built by PCR amplification of the DNA using the vector pET30-497C-T2 as template, the 5' specific primer 497c-cds7, which permitted to eliminate most of the b domain and to preserve the first C-C bridge, and the 3' specific primer 497C-cds4.

TABLE 2

| Primer | SEQ ID NO | Sequence |
|---|---|---|
| 497c-cds7 | 11 | 5'GACGACGACAAGATGCAGCGCAGCCTGAGCTGC 3' |
| 497c-cds-4 | 10 | 3'GAGGAGAAGCCCGGTctccagcgatgattcccatgtt 5' |

497C-T4

The truncated 497C-T4 was built by PCR amplification of the DNA using the vector pET30-497C-T2 as template, the 5' specific primer 497c-cds9, which permitted to eliminate the first C-C bridge, the b and c domains, and to preserve the d1 domain, and the 3' specific primer 497C-cds4.

TABLE 3

| Primer | SEQ ID NO | Sequence |
|---|---|---|
| 497c-cds9 | 12 | 5'GACGACGACAAGATCCCCCCCAGCTGCTGCATG 3' |
| 497c-cds-4 | 10 | 3'GAGGAGAAGCCCGGTctccagcgatgattcccatgtt 5' |

497C-T5

The truncated 497C-T4 was built by PCR amplification of the DNA using the vector pET30-497C-T2 as template, the 5' specific primer 497c-cds11, which permitted to eliminate the first and the second C-C bridges, the b, c and d1 domains, and to preserve the linear sequence corresponding to the d2 and e domains, and the 3' specific primer 497C-cds4.

TABLE 4

| Primer | SEQ ID NO | Sequence |
|---|---|---|
| 497c-cds11 | 13 | 5' GACGACGACAAGATGAACGAAACTGATTGTAATCCCC 3' |
| 497c-cds-4 | 10 | 3'GAGGAGAAGCCCGGTctccagcgatgattcccatgtt 5' |

For the N-terminal His-Tag and the C-terminal tail, the constructs were obtained using the following primers which totally eliminated the sequence of the protein 497C-T2.

TABLE 5

| Primer | SEQ ID NO | Sequence |
|---|---|---|
| Pet30 cds1 | 14 | 5'GACGACGACAAGATGGACCGGGCTTCTCCT 3' |
| pet30 cds2 | 15 | 5'GAGGAGAAGCCCGGTCTAGTTATTGCTCAGCGG 3' |

The amplified products corresponding to the truncated forms 497C-T3, 497C-T4, 497C-T5, and the C-terminal tail were cloned and produced as described for the protein 497C-T2.

EXAMPLE 3

Test of Inhibition of Endothelial Cell Proliferation by 497-T2 In Vitro

Cell Culture

HUVEC cells were cultured to confluency in complete EGM2-MV medium (Cambrex) at 37° C. and in 5% $CO_2$ humidified atmosphere. Cells were then collected by trypsine-EDTA digestion (Versene, Eurobio). After 5 min, the enzymatic reaction was stopped by adding 3 ml of the culture medium containing 5% FCS. Cells were then centrifuged at 220 g for 10 min at room temperature, washed twice with 5 ml of culture medium, suspended in complete culture medium, counted and adjusted to 50 000 cells/ml. One hundred μL per well were then distributed to a 96-well cell culture grade micro-plate (5 000 cells/well) and incubated with different concentrations of the purified protein 497C-T2 in Tris-HCl 20 mM buffer (pH 8), containing 150 mM NaCl and urea 2M; this buffer was used as control.

After 42 hrs at 37° C., cell proliferation was measured using thiazolyl blue tetrazolium bromide (MTT) method. Briefly, MTT (Sigma) was dissolved in PBS at 5 mg/ml, the solution was filtered (0.22 μm) and 10 μl were added to each well of the 96-well micro-plates. After 3 hrs of incubation at 37° C., 5% $CO_2$ humidified atmosphere, the micro-plates were centrifuged at 220×g for 10 min, the supernatant was discarded, and the crystals dissolved by the addition of 100 μl of DMSO to each well. The optical density (OD) at 570 nm was then measured using μQuant micro-plate reader (Bio-Tek Instrument gmbh, Colmar, France) coupled to the KC4 (Bio-Tek) software. The OD was corrected by subtracting blank-well OD values (the OD values obtained from wells without cells), and the inhibition of cell proliferation was measured relative to control (OD obtained from wells with untreated HUVEC representing the maximal proliferative response, i.e. 100%)

As shown in FIG. 1, protein 497C-T2 inhibited human endothelial cell proliferation in a dose dependent manner. This inhibition represented 77% at 122 μg (i.e. 5 μM) of protein 497C-T2. .

EXAMPLE 4

Inhibition of In Vitro Angiogenesis by 497-T2, 497C-T3, 497C-T4 and 497C-T5

The purified proteins 497C-T2 497C-T3, 497C-T4 and 497C-T5 were tested in vitro on angiogenesis of HUVEC induced by FGF2 and VEGF on Matrigel.

Figure 2A:
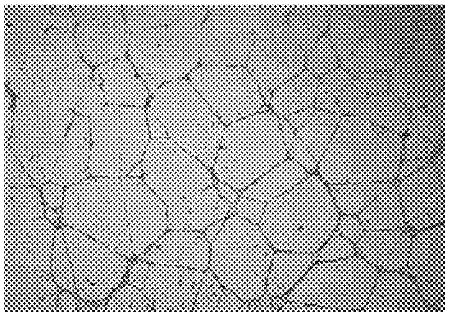
Figure 2B:
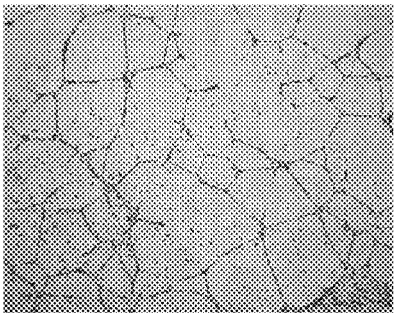
Figure 2C:
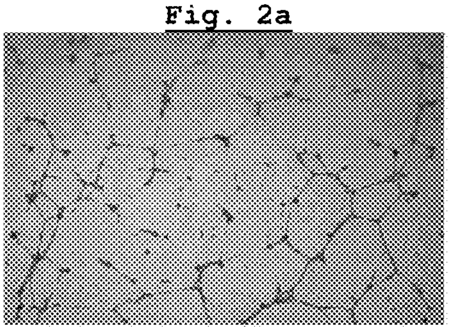
Figure 2D:
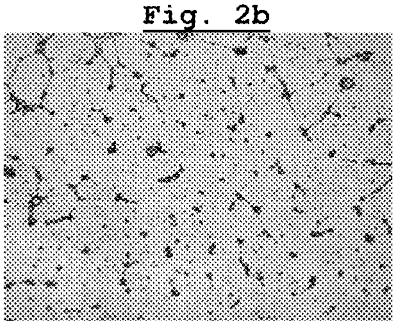
Figure 2E:
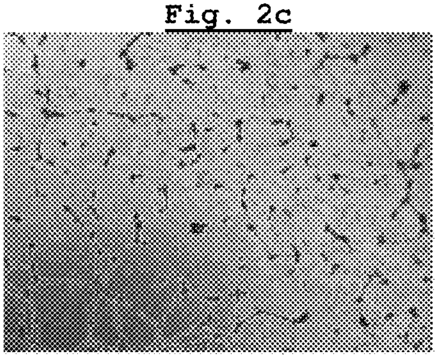

24 wells plates were prepared with 250 μL of BD Matrigel™/well and then incubated 30 minutes in incubator. HUVEC cells were then prepared as described in example 3 and 70 000 cells were seeded per well and incubated with different concentrations of the purified protein 497C-T2, 497C-T3, 497C-T4 or 497C-T5 in Tris-HCl 20 mM buffer (pH 8), containing 150 mM NaCl and urea 2M; this buffer was used as control:

FIG. 2*a*: Control (Buffer Urea 2M)
FIG. 2*b*: 497C-T2 6.5 μg/mL (0.27 μM)
FIG. 2*c*: 497C-T2 13 μg/mL (0.54 μM)
FIG. 2*d*: 497C-T2 26 μg/mL (1.08 μM)
FIG. 2*e*: 497C-T2 48 μg/mL (2 μM)
FIG. 2*f*: 497C-T3 51 μg/mL (2.55 μM)
FIG. 2*g*: 497C-T4 55 μg/mL (3.18 μM)
FIG. 2*h*: 497C-T5 56 μg/mL (3.35 μM)
FIG. 2*i*: C-terminal tail 53 μg/mL (4.14 μM)

As shown in FIGS. 2*b*, 2*c*, 2*d* and 2*e*, protein 497C-T2 inhibited in vitro angiogenesis in a dose-dependent manner.

Figure 2F:
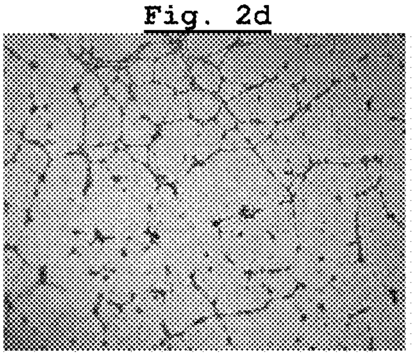
Figure 2G:
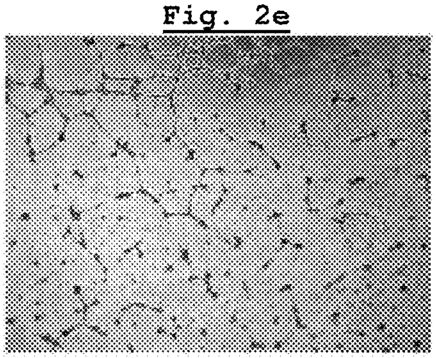
Figure 2H:
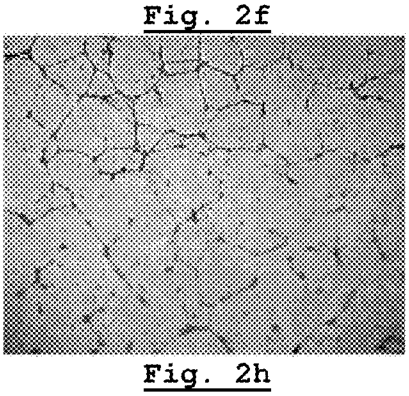
Figure 2I:
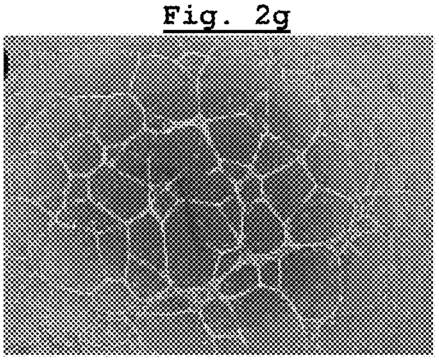

Moreover, as shown in FIGS. 2*f*, 2*g* and 2*h*, the truncated forms 497C-T3, 497C-T4 and 497C-T5 showed different levels of activity: 497C-T3 (FIG. 2*f*) and 497C-T4 (FIG. 2*g*) were almost as efficient as 497C-T2 for the anti-angiogenic activity, suggesting that the a, b and c LEL domains are not necessary for the anti-angiogenic activity of protein 497C-T2. To the contrary, 497C-T5 (FIG. 2*h*) showed only a residual inhibitory activity, while the C-terminal tail was totally inactive (FIG. 2*i*).

EXAMPLE 5

Inhibition of the Migration of Human Endothelial Cells by 497-T2, 497C-T3, 497C-T4 and 497C-T5

Figure 3A:
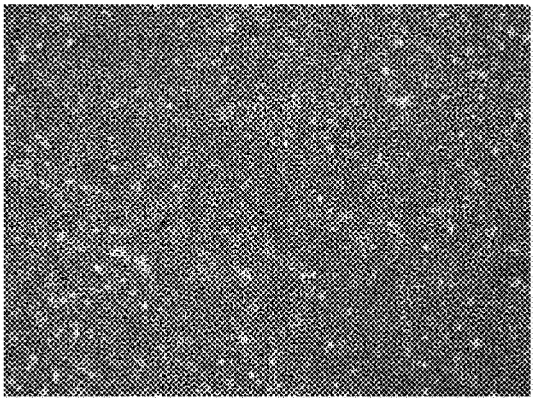
Figure 3B:
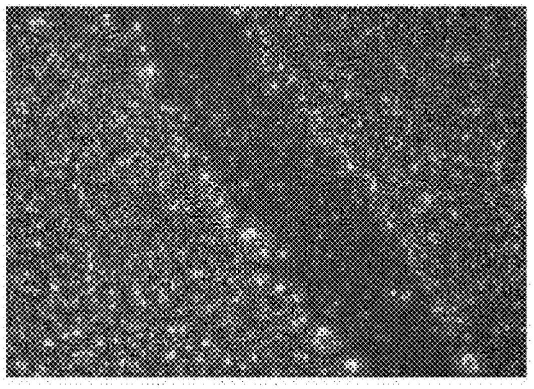
Figure 3C:
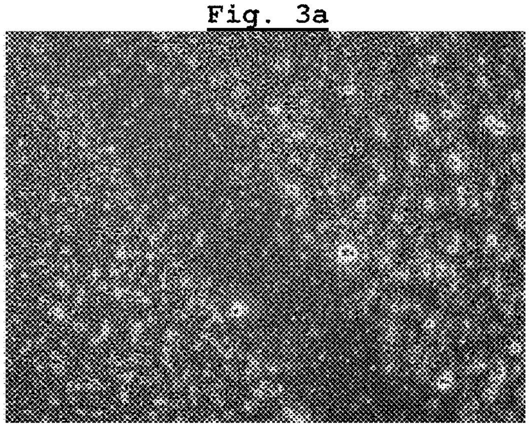
Figure 3D:
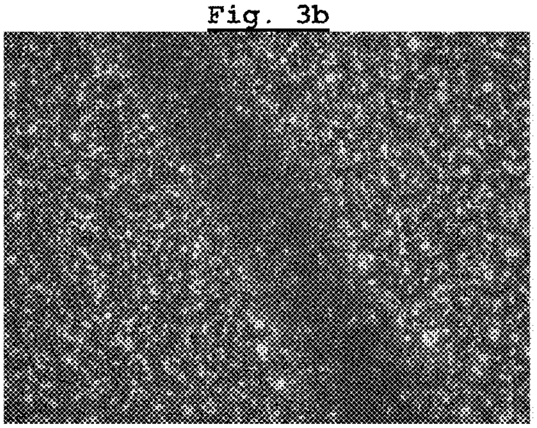
Figure 3E:
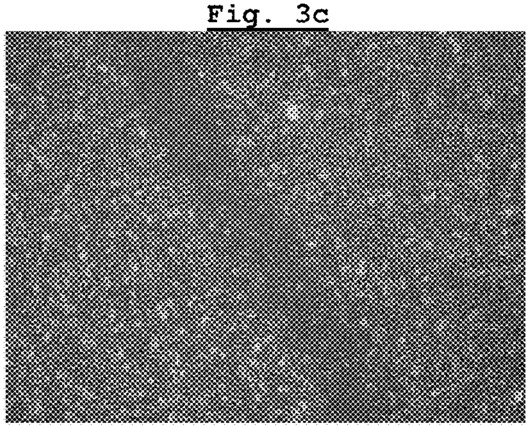
Figure 3F:
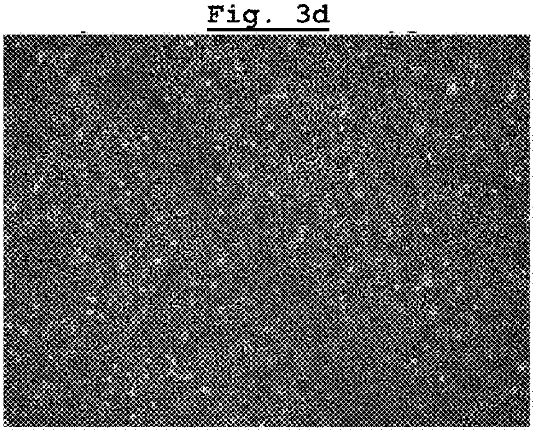
Figure 3G:
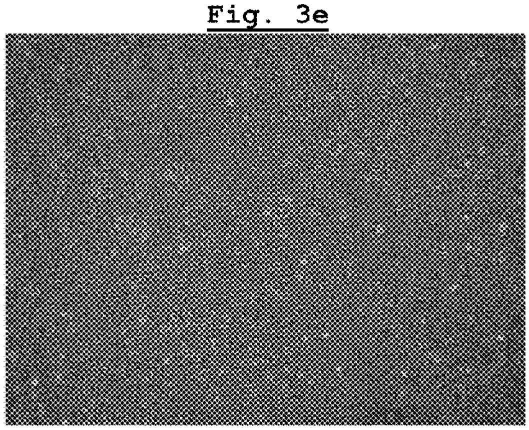

Cell migration was tested by the wound assay described by Sato and Rifkin (J. Cell Biol. 1988; 107:1199) with few modifications. HUVEC grown in growth medium EGM-2MV (Cambrex) were seeded in 24-well plates at 80 000 cells per well in 500 μL of growth medium and grown to confluence at 37° C. in a humidified atmosphere containing 5% $CO_2$. Cells were scrapped with a plastic tip on one line only. After wounding, the culture medium was changed for fresh medium (control, FIG. 3*a*) or fresh medium supplemented with:

FIG. 3*b*: 497C-T2 20 μg/mL (0.83 μM)
FIG. 3*c*: 497C-T2 40 μg/mL (1.66 μM)
FIG. 3*d*: 497C-T3 48 μg/mL (2.4 μM)
FIG. 3*e*: 497C-T4 60 μg/mL (3.52 μM)
FIG. 3*f*: 497C-T5 61 μg/mL (3.65 μM)
FIG. 3*g*: C-terminal tail 63 μg/mL (4.92 μM)

After 18 hours of culture, cells were observed and photographed under the inverted microscope (Analysis, Olympus, Rungis, France).

As shown in FIGS. 3*b* and 3*c*, protein 497C-T2 inhibited human endothelial cells migration in a dose dependent manner.

Moreover, as shown in FIGS. 3*d*, 3*d*, 3*e* and 3*f* the truncated forms 497C-T3, 497C-T4 and 497C-T5 showed different levels of activity. The truncated form 497C-T3 inhibited cell migration similarly to the protein 497C-T2 (FIG. 3*d*). To the contrary, the truncated form 497C-T4 (FIG. 3*e*) was less active than 497C-T2, 497C-T5 (FIG. 3*f*) showed very limited anti-migratory activity, and the C-terminal tail (FIG. 3*g*) was totally inactive. These results thus suggested that the a and b LEL domains are not necessary for the anti-migratory activity of protein 497C-T2.

EXAMPLE 6

Expression of Protein 497C in Tumor Samples

A number of different human tumor samples were screened for the expression of the gene 497C. For each pathological sample, the periphery of the tumor was separated from the core of the tumor, and the expression of the gene 497C in these two area was compared after mRNA extraction followed by RT-PCR.

Kidney Tumor Samples 19 pathological biopsies from kidney tumors were analysed. In 13 out of 19 patients, the expression of 497C was much higher in the core than in the periphery of the tumor.

Lung Tumor Samples 40 pathological biopsies from human lung tumors were analysed. In 37 out of 40 patients, the expression of 497C was much higher in the periphery than in the core of the tumor. There was also a close relationship between the level of expression of 497C at the periphery of the tumor and the patient's nod status (i.e. the metastasis potential). The anatomical examination of the samples also revealed that the periphery of the tumor was much more vascularised than the core of the tumor (as established for lung cancer in general).

Colon Tumor Samples 33 pathological biopsies from human colon tumors were analysed. In 25 out of 33 patients, the expression of 497C was much higher in the periphery than in the core of the tumor.

EXAMPLE 7

Test of 497C-T2 on NCI H460 Human Tumor in Swiss Nude Mice In Vivo

Preparation of NCI H460 Cells

NCI H460 cells were cultured as adherent cells in complete RPMI 1640 medium (Ref. CM1RPM08-01, batch No. 623615, Eurobio, France) containing 2 mM L-Glutamine, adjusted to 4.5 g/L glucose (Ref. G7528, batch No. 033K0121, Sigma, France) and supplemented with 10 mM HEPES (Ref. H0887, batch No. 113K2338, Sigma, France), 1.0 mM sodium pyruvate (Ref. CSTVAT00-0U, batch No. 520818, Sigma, France) and 10% fetal calf serum (FCS; Ref. CVFSVF00-01, batch No. S13021, Eurobio, France) under a 37° C., 5% $CO_2$ humidified atmosphere. They were amplified in 75 $cm^2$-flasks to reach $90\times10^6$ cells.

At D0, NCI H460 cells (human lung carcinoma) were collected from 75 $cm^2$-flasks by removing the medium and adding 3 ml of trypsine-EDTA (Ref. CEZTDA00-0U, batch No. 633920, Eurobio, France). After 5 min of incubation at 37° C., cells were detached from the plastic and the enzymatic reaction was stopped by adding 3 ml of RPMI 1640 medium containing 10% fetal calf serum. Cells were then centrifuged at 700 g for 5 min at room temperature. They were resuspended in serum-free RPMI 1640 culture medium containing L-Glutamine (2 mM), glucose (4.5 g/l), sodium pyruvate (1 mM) and buffered with HEPES (10 mM). Cells were counted and the number of viable NCI H460 cells was >99%. The number of cells was then adjusted to $25.10^6$ cells/ml in serum-free medium.

Tumor Induction

Thirty healthy female Swiss Nude mice were anesthetized by IP injection of Ketamine-Xylazine (80 mg/kg-12 mg/kg; Ref. K-113, Sigma, France). NCI H460 cells (5.10 cells/ mouse in 200 μL of serum-free medium) were then implanted subcutaneously in the right flank of each mouse.

Treatment Schedule

At D12 post-implantation of the NCI H460 cells, the thirty mice were randomized into six groups of 5 mice. Tumor volumes had reached 228 to 468 $mm^3$ and mean tumor volumes were not statistically different between groups after randomization.

The treatment schedule, starting D12 and ending D28, is summarized in Table 6:

- Animals of group 1 were treated with the vehicle solution (Batch C): Tris-HCl pH 7.5, 2M Urea, 150 mM NaCl, 0.1 mM $CaCl_2$,
- Animals of group 2 were treated with a solution of cisplatin in physiological serum 0.5 ml/mL (CDDP, cis-diamine-platinum(II)dichloride, Ref. P4394, batch No. 014K0993, Sigma, France, purity 100%, MW. 300),
- Animals of groups 3, and 4 were treated with the vehicle solution supplemented with 1 mg/mL of the test substance 497C-T2 (Batch A),
- Animals of group 5 were treated with the vehicle solution supplemented with 1 mg/mL of the test substance 497C-T2 (Batch A), and further received CDDP.

CDDP was resuspended in sterile physiological serum at a concentration of 0.5 mg/mL and injected IP at a concentration of 5 mg/kg at a volume of 10 mL/kg, according to the treatment schedule Q2DX8.

Mice were observed for 2 h post-injection. Ketamine/Xylazine (80 mg/kg-12 mg/kg; Ref. K-113, Sigma, France) was used to anaesthetize the animals before sacrifice by cervical dislocation.

Monitoring of the Mice

Animals have been observed daily. Modification in animal behavior has been reported in the laboratory notebook. Body weights and tumor volumes were recorded every two days until the end of the experiment.

Data outlined below were calculated:

- Tumor growth curves were drawn using the mean tumor volumes (MTV),
- Mean Relative tumor volume (MRTV) was calculated as the ratio between the MTV at time t and the volume at the time of injection (t=D12),
- Tumor growth inhibition (T/C, %) was evaluated as the ratio of the median tumor volumes of treated groups versus vehicle group.

TABLE 6

| Group | Animals n | Treatment | Administration route | Treatment dose (mg/kg/adm) | Administration volume | Treatment schedule |
|---|---|---|---|---|---|---|
| 1 | 5 | Vehicle (Batch C) | IP | 0 | 10 ml/kg | Q2DX8 |
| 2 | 5 | Cisplatin | IP | 5 | | Q2DX8 |
| 3 | 5 | 497C-T2 (Batch A) | IP | 10 | | Q2DX8 |
| 4 | 5 | 497C-T2 (Batch A) | IP | 10 | | Q1DX16 |
| 5 | 5 | 497C-T2 (Batch A) & | IP | 10 | | Q2DX8 |
| | | Cisplatin | | 5 | | Q2DX8 |
| 6 | 5 | 497C-T2 (Batch B) & | IP | 18 | | Q2DX8 |
| | | Cisplatin | | 5 | | Q2DX8 |

TABLE 7

Mean body weight (MBW) of mice bearing NCI H-460 tumors treated with the vehicle, CDDP at 5 mg/kg (schedule Q2DX8, G2), 497C-T2 at 10.0 mg/kg (schedule Q2DX8, G3), 497C-T2 at 10.0 mg/kg (schedule Q1DX16, G4), combined 497C-T2 at 10.0 mg/kg and CDDP at 5 mg/kg (schedule Q2DX8, G5), and combined 497C-T2 at 18.0 mg/kg and CDDP at 5 mg/kg (schedule Q2DX8, G6) at D12 and D28.

| Group | Test substance | Treatment dose (mg/kg) | MBW at D12 (g) | MBW at D28 (g) | MBWC D12-D28 (g) |
|---|---|---|---|---|---|
| 1 | Vehicle-Batch C | 0 | 22.53 ± 0.79 | 23.72 ± 0.72 | 1.18 ± 0.79 |
| 2 | Cisplatin | 5.00 | 21.29 ± 0.41 | 18.74 ± 1.59 | −2.55 ± 1.83 |
| 3 | 497C-T2-Batch A | 10.0 | 24.06 ± 1.59 | 25.70 ± 1.12 | 1.63 ± 1.59 |
| 4 | 497C-T2-Batch A | 10.0 | 21.76 ± 1.63 | 23.68 ± 2.17 | 1.91 ± 1.36 |
| 5 | 497C-T2-Batch A + | 10.0 | 23.28 ± 2.03 | 20.19 ± 0.66 | −3.09 ± 2.68 |
| | Cisplatin | 5.00 | | | |
| 6 | 497C-T2-Batch B + | 18.0 | 23.08 ± 1.78 | 19.00 ± 2.00 | −4.08 ± 0.71 |
| | Cisplatin | 5.00 | | | |

- Animals of group 6 were treated with the vehicle solution supplemented with 1.8 mg/mL of the test substance 497C-T2 (Batch B), and further received CDDP.

All solutions were injected IP. Injections in groups 1, 2, 3, 5 and 6 were performed according to the schedules Q2DX8, i.e. 1 quantity every two days, eight times. Injections in group 4 were performed according to the schedules Q1DX16, i.e. 1 quantity every day, sixteen times.

Statistical Studies

Statistical analyses of tumor volumes (V), time to reach 'V', tumor-doubling time (DT), relative tumor volume (RTV) and tumor growth inhibition (T/C) were performed for all groups. Data are expressed as mean±SD. Groups of data were normally distributed. Univariate analysis were performed to assess differences between groups. Statistical significance was then determined using the Student's t test. A $P<0.05$ was considered as statistically significant. The Statistical analysis was performed using XLSTAT (Addinsoft, France).

Body Weight Monitoring

As shown in table 7, the vehicle had no impact on the body weight: mouse behavior and body weight gain were normal and no animal died prematurely. No toxicity was observed during the course of the treatment with the test substance 497C-T2 at both doses tested (10 and 18 mg/kg). In contrast, an important toxicity was observed in groups 2, 5 and 6 treated with CDDP (from −12 to −18% body weight loss; $p<0.05$).

Figure 4:
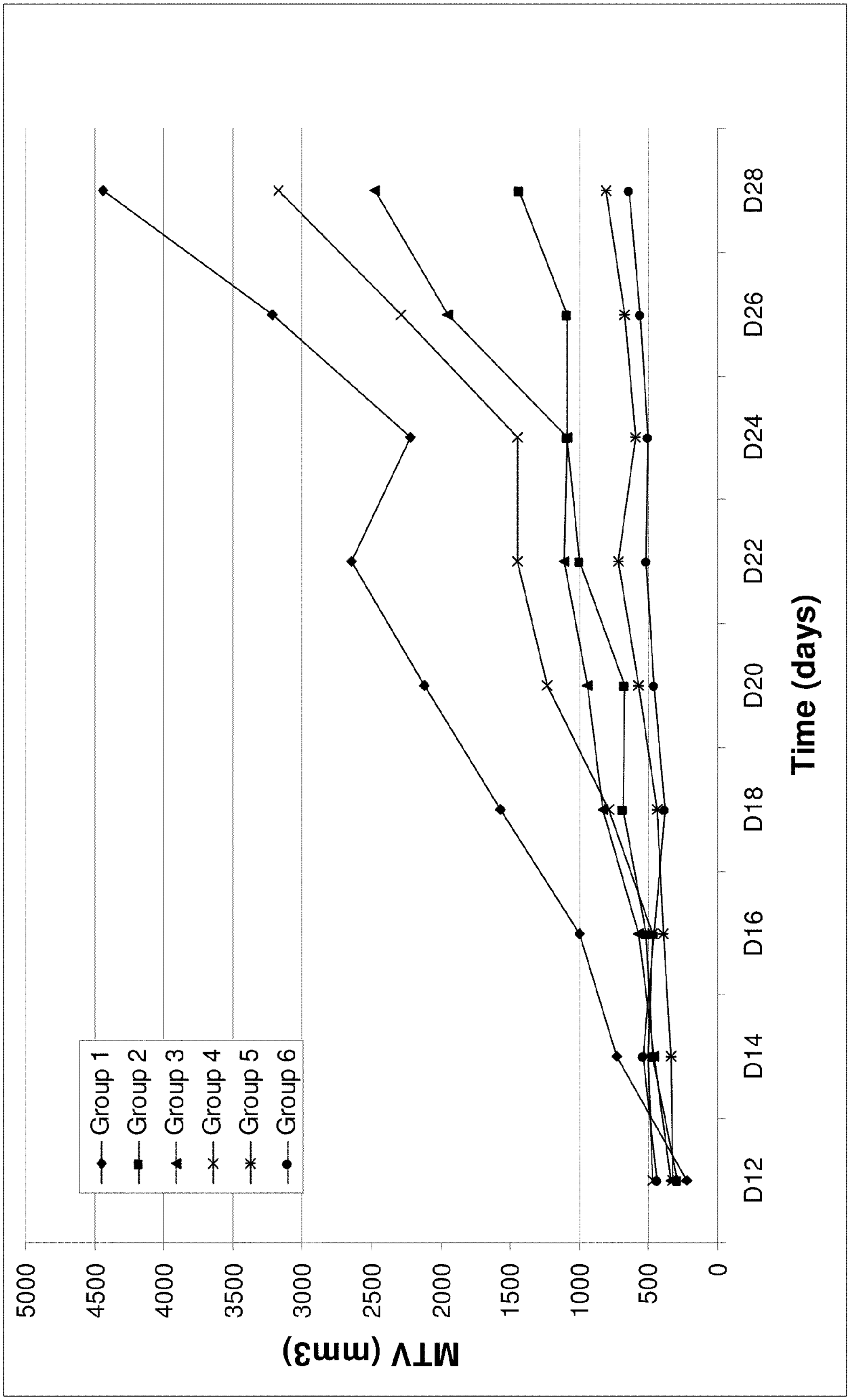
FIG. 4 is a graph representing Mean Tumor Volume ($mm^3$) versus time (days) for different groups of mice treated according to example 7.
Figure 5:
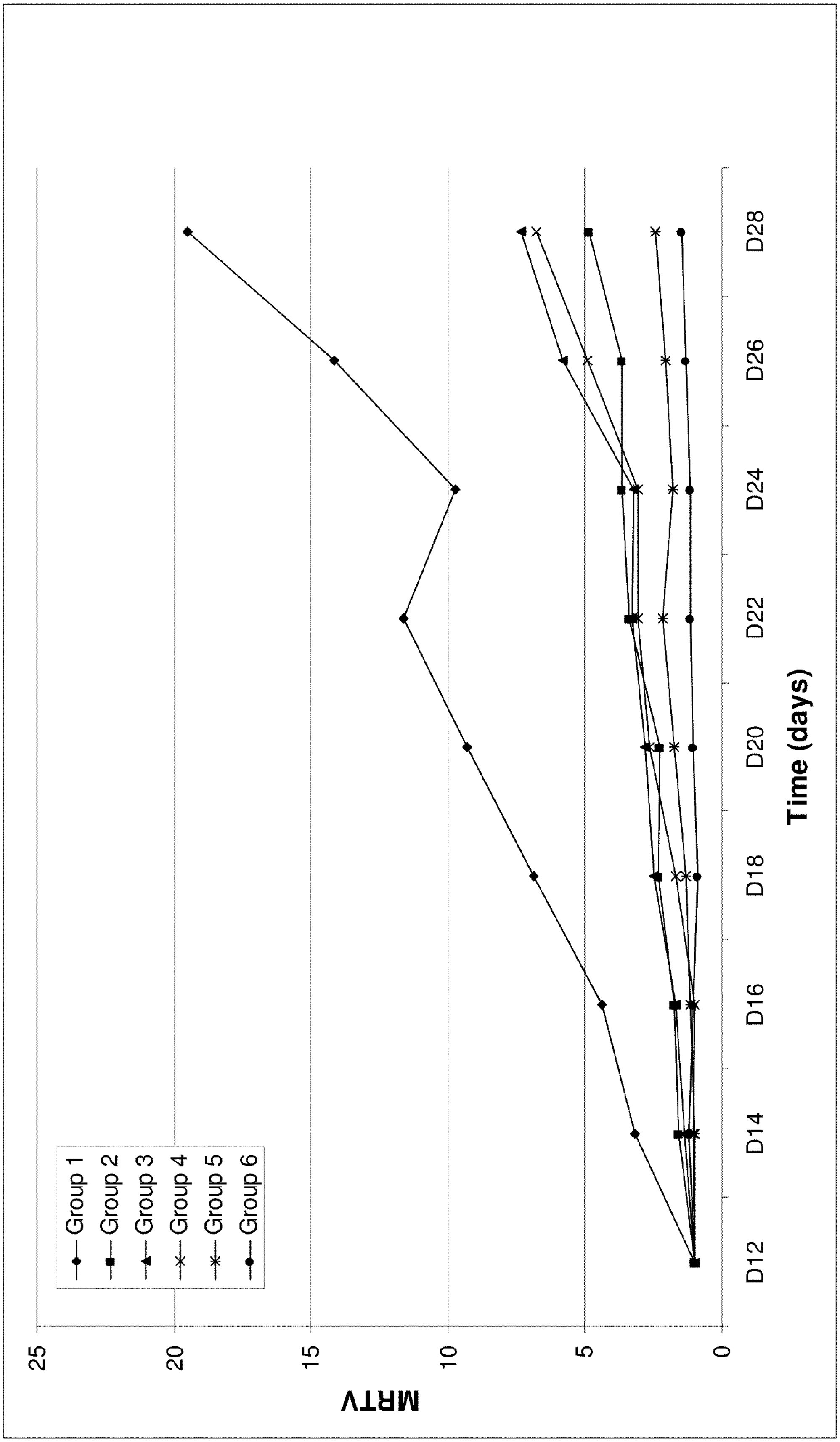
FIG. 5 is a graph representing Mean Relative Tumor Volume (without unit) versus time (days) for different groups of mice treated according to example 7.

The results of mean tumor volume (MTV), mean relative tumor volume (MRTV), tumor volume and tumor growth parameters are shown in FIGS. 4, 5 and in Table 8 and Table 9.

As shown in table 8, the MTV was decreased at D28 in mice of group 2 treated with CDDP (1440±1097 $mm^3$) compared to mice of the vehicle group 1 (4441±1135 $mm^3$). The MTV at D28 was also decreased in groups 3 and 4 treated with the test substance 497C-T2 at 10 mg/kg with 1 injection per day (2482±2075 $mm^3$) and 1 injection every other day (3167±1681 $mm^3$), respectively. A massive reduction of the MTV was observed in animals from group 5 (807±692 $mm^3$) and group 6 (639±416 $mm^3$) compared to group 1, the vehicle treated animals (4441±1135 $mm^3$).

The T/C ratio, which is a parameter of tumor growth inhibition, represented 32% in mice from group 2 at D28 demonstrating that CDDP reduces by 68% tumor size compared to the vehicle-treated group 1. T/C was 56% in mice from for group 3 and 71% in mice from group 4, revealing a moderate anti-tumoral activity of the test substance when used as a monotherapy. When combined with CDDP however, T/C fell to 18% and 14% in mice from groups 5 and 6, respectively. This demonstrates that 497C-T2 has a potent anti-tumoral activity when combined a cytotoxic agent such as CDDP.

The tumor size doubling time (DT) was 1.23±0.49 days in the vehicle-treated group 1. The DT increased 4-fold in mice of group 2 treated with CDDP alone (5.12±2.89 days). For groups 3 and 4, the DT (4.08±1.4 and 5.9±1.21 days, respectively) was similar to that of group 2. This indicates that 497C-T2 is as potent as CDDP to reduce tumor activity when used as monotherapy. But most importantly, bi-therapy using 497C-T2 and CDDP increased 20-fold DT in animals from groups 5 and 6 (25.02±29.89 and 20.07±9.28 days, respectively) compared to the DT measured in mice from the vehicle-treated group 1. This further confirms the potent anti-tumoral activity of the tested substance 497C-T2 when used alone or in combination with CDDP.

As shown in table 9, MRTV measures confirmed that animal of group 6 presented the strongest decrease of the tumor volume, at both concentration tested (group 5,6). Treatment with 497C-T2 alone led to a MRTV at D28 of 7.37 (group 3) or 6.76 (group 4) and treatment with cisplatin led to a MRTV of 4.88 (group 2).

All these results confirm that 497C-T2 is a potent anti-tumor agent, either used alone or in a synergistic combination with cisplatin.

EXAMPLE 8

Test of 497C-T2 on Non-Small Human Cell Lung Cancer (CALU-6) Xenograft Model in Swiss Nude Mice In Vivo

Preparation of CALU-6 cells

CALU-6 cells were cultured as adherent cells in complete EMEM medium (Ref. CM1MEM18-01, batch No. 462502, Eurobio, France) 10% fetal calf serum (FCS; Ref. CVFSVF00-01, batch No. S13021, Eurobio, France) under a 37° C., 5% $CO_2$ humidified atmosphere. They were amplified in 75 $cm^2$-flasks to reach $90\times10^6$ cells.

At D0, CALU-6 cells (human lung carcinoma) were collected from 75 $cm^2$-flasks by removing the medium and adding 3 ml of trypsine-EDTA (Ref. CEZTDA00-0U, batch No. 633920, Eurobio, France). After 5 min of incubation at 37° C., cells had detached from the plastic and the enzymatic reaction was stopped by adding 3 ml of EMEM medium containing 10% fetal calf serum. Cells were then centrifuged at 700 g for 5 min at room temperature. They were resuspended in serum-free EMEM culture medium. Cells were counted and viability assessment by Trypan Blue exclusion (Ref. CSTCOL03-OU, batch No. 434511, Eurobio, France). The number of viable CALU-6 cells was >99%. The number of cells was then adjusted to $25\times10^6$ cells/ml in serum-free medium.

TABLE 8

Monitoring of human NCI H460 tumor growth in Nude mice after IP treatment with vehicle, 497C-T2 (10 mg/kg and 18 mg/kg) and CDDP (5 mg/kg).

| Group | Test substance | Treatment dose (mg/kg) | MTV at D14 ($mm^3$) | MTV at D24 ($mm^3$) | MTV at D28 ($mm^3$) | T/C at D14 (%) | T/C at D24 (%) | T/C at D28 (%) | DT (days) |
|---|---|---|---|---|---|---|---|---|---|
| 1 | Vehicle-Batch C | 0 | 999.64 ± 443.46 | 3222.36 ± 494.51 | 4440.68 ± 1135.16 | 100 | 100 | 100 | 1.23 ± 0.49 |
| 2 | CDDP | 5.0 | 513.35 ± 333.36 | 1083.74 ± 899.44 | 1440.18 ± 1097.29[a] | 51.53 | 33.63 | 32.43 | 5.12 ± 2.89 |
| 3 | 497C-T2-Batch A- | 10.0 | 571.00 ± 306.73 | 1955.02 ± 1687.55 | 2481.61 ± 2075.18 | 57.12 | 60.67 | 55.88 | 4.08 ± 1.4 |
| 4 | 497C-T2-Batch A- | 10.0 | 468.85 ± 250.00 | 2289.22 ± 1170.70 | 3167.34 ± 1680.99 | 46.90 | 71.04 | 71.32 | 5.9 ± 1.21 |
| 5 | 497C-T2-Batch A-+CDDP | 10.0<br>5.0 | 388.79 ± 315.14 | 671.93 ± 570.47[a] | 807.43 ± 692.22[a,c] | 38.89 | 20.85 | 18.18 | 25.02 ± 29.89 |
| 6 | 497C-T2-Batch B-+CDDP | 18.0<br>5.0 | 459.45 ± 166.55[a] | 561.71 ± 218.34[a,b,c,d] | 638.74 ± 415.53[a,b,c,d] | 45.96 | 17.43 | 14.38 | 20.07 ± 9.28 |

MTV: mean tumor volume;
T/C: treated/vehicle tumor volume ratio;
DT: doubling time of tumor volume.
[a]p < 0.05 vs G1
[b]p < 0.05 vs G2
[c]p < 0.05 vs G3
[d]p < 0.05 vs G4.

TABLE 9

Mean relative tumor volume (MRTV) of animals bearing the NCI H460 tumor and treated with vehicle (Group 1), CDDP alone (Group 2), 497C-T2 administered every other day (Group 3) or once daily (Group 4), and CDDP combined with 497C-T2 at the lower (Group 5) and higher dose (Group 6).

| | D12 | D14 | D16 | D18 | D20 | D22 | D24 | D26 | D28 |
|---|---|---|---|---|---|---|---|---|---|
| Group 1 | 1.00 | 3.18 | 4.39 | 6.87 | 9.28 | 11.61 | 9.73 | 14.15 | 19.50 |
| Group 2 | 1.00 | 1.59 | 1.74 | 2.30 | 2.29 | 3.39 | 3.67 | 3.67 | 4.88 |
| Group 3 | 1.00 | 1.37 | 1.70 | 2.46 | 2.81 | 3.30 | 3.22 | 5.80 | 7.37 |
| Group 4 | 1.00 | 1.08 | 1.00 | 1.69 | 2.63 | 3.08 | 3.08 | 4.89 | 6.76 |
| Group 5 | 1.00 | 1.01 | 1.18 | 1.34 | 1.75 | 2.18 | 1.80 | 2.04 | 2.45 |
| Group 6 | 1.00 | 1.24 | 1.06 | 0.89 | 1.07 | 1.18 | 1.17 | 1.30 | 1.48 |

Tumor Induction

Thirty healthy female Swiss Nude mice were anesthetized by IP injection of Ketamine-Xylazine (80 mg/kg-12 mg/kg; Ref. K-113, Sigma, France). CALU-6 cells $5\times10^6$ cells/mouse in 200 µl of serum-free medium) were then implanted subcutaneously in the right flank of each mouse. Mice were observed for 2 h post-implantation.

Treatment Schedule

At D12 post-implantation of the CALU-6 cells, the thirty mice were randomized into six groups of 5 mice. Tumor volumes had reached 228 to 468 $mm^3$ and mean tumor volumes were not statistically different between groups after randomization.

The treatment schedule, starting D12 and ending D28, is summarized in Table 10.

- Animals of group 1 were treated with the vehicle solution (Tris-HCl pH 7.5, 2M Urea, 150 mM NaCl, 0.1 mM $CaCl_2$) (Batch C);
- Animals of group 2 were treated with a solution of cisplatin in physiological serum 0.5 mh/mL(CDDP, cis-diamine-platinum(II)dichloride, Ref. P4394, batch No. 014K0993, Sigma, France, purity 100%, MW. 300),
- Animals of group 3 were treated with the vehicle supplemented with the test substance 497C-T2 at a dose of 10 mg/kg.
- Animals of group 4 were treated with the vehicle supplemented with the test substance 497C-T2 at a dose of 10 mg/kg, and further received CDDP.

Injections in groups 1, 2, 3 and 4 were performed according to the schedules Q2DX8, i.e. 1 quantity every two days, eight times.

CDDP was resuspended in sterile physiological serum at a concentration of 0.5 mg/mL and injected IP at a concentration of 5 mg/kg at a volume of 10 mL/kg, according to the treatment schedule Q2DX8.

Mice were observed for 2 hours post-injection. Ketamine/Xylazine (80 mg/kg-12 mg/kg; Ref. K-113, Sigma, France) was used to anaesthetize the animals before sacrifice by cervical dislocation. For all animals, the tumor size was measured twice a week with calipers. The tumor volume ($mm^3$) was measured according to the formula:

$$(\text{length}\times\text{width}^2)/2(4).$$

Statistical Studies

Mean tumor volumes (MTV), mean relative tumor volume (MRTV) and tumor growth inhibition (T/C) were calculated as for example 7.

Body Weight

As shown in table 11, the vehicle had no impact: mouse behavior and body weight gain were normal and no animal died prematurely (excepted mouse 5 of group 1). No toxicity was observed during the course of the treatment with the test substance 497C-T2 at the dose of 10 mg/kg, a slight body weight gain was observed (+1.44 g).

In contrast, an important toxicity was observed in groups 2, 4 treated with CDDP. (12.6% and 8.7% body weight loss respectively). The difference between group 1 versus 2 and 4 and group 3 versus 2 and 4 was statistically significant ($p<0.0001$) but the difference between group 2 and 4 was not statistically significant.

TABLE 10

| Group | Animals n | Treatment | Administration route | Treatment dose (mg/kg/adm) | Administration volume | Treatment schedule |
|---|---|---|---|---|---|---|
| 1 | 5 | Vehicle | IP | 0 | 10 ml/kg | Q2DX8 |
| 2 | 5 | Cisplatin | IP | 5 | | Q2DX8 |
| 3 | 5 | 497C-T2 | IP | 10 | | Q2DX8 |
| 4 | 5 | 497C-T2 & | IP | 10 | | Q2DX8 |
| | | Ciplatine | | 5 | | Q2DX8 |

TABLE 11

Mean body weight (MBW) of mice bearing CALU-6 tumors treated with the vehicle, CDDP at 5 mg/kg (schedule Q2DX8, G2), 497C-T2 at 10.0 mg/kg (schedule Q2DX8, G3), combined 497C-T2 at 10.0 mg/kg and CDDP at 5 mg/kg (schedule Q2DX8, G4) at D12 and D28.

| Group | Test substance | Treat-ment dose (mg/kg) | MBW at D12 (g) | MBW at D28 (g) | MBWC D12-D28 (g) |
|---|---|---|---|---|---|
| 1 | Vehicle | 0 | 22.35 ± 1.17 | 24.40 ± 1.14 | +2.04 |
| 2 | Cisplatin | 5.00 | 21.39 ± 0.85 | 18.69 ± 1.97 | −2.70 |
| 3 | 497C-T2 | 10.0 | 21.67 ± 1.32 | 23.11 ± 1.97 | +1.44 |
| 4 | 497C-T2 + Cisplatin | 10.0 & 5.00 | 21.94 ± 0.74 | 19.84 ± 1.89 | −2.11 |

Figure 6:
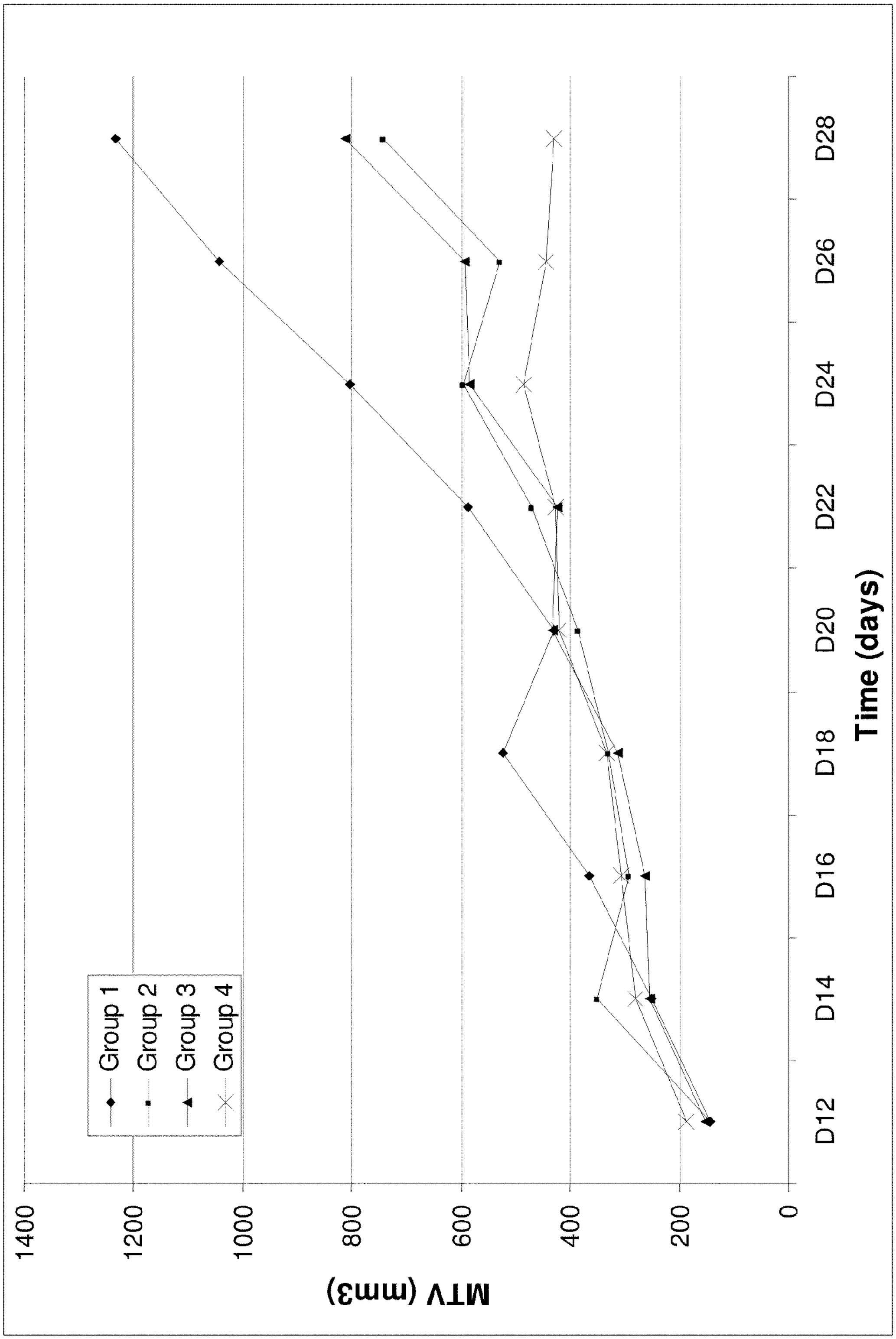
FIG. 6 is a graph representing Mean Tumor Volume ($mm^3$) versus time (days) for different groups of mice treated according to example 8.
Figure 7:
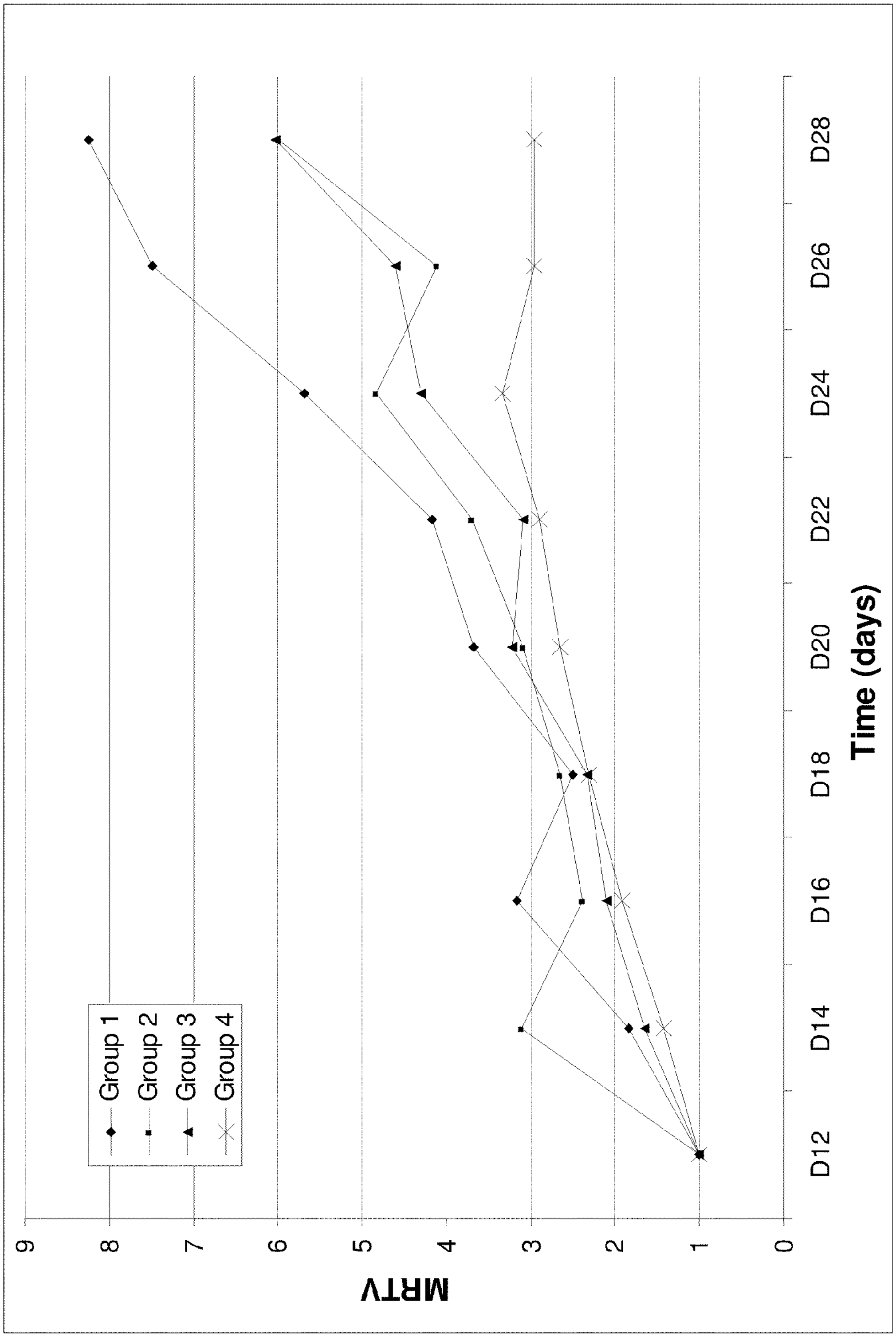
FIG. 7 is a graph representing Mean Relative Tumor Volume (without unit) versus time (days) for different groups of mice treated according to example 8.

The results of mean tumor volume (MTV), mean relative tumor volume (MRTV), tumor volume and tumor growth parameters are shown in FIGS. 6, 7 and in Table 12 and Table 13.

The MTV was decreased at D28 in mice of group 2 treated with CDDP (742.44±215.85 $mm^3$) compared to mice of the vehicle group 1 (1 233.44±663.82 $mm^3$). The MTV at D28 was also decreased in group 3 treated with the test substance 497C-T2 at 10 mg/kg with 1 injection per two days (813.70±439.00 $mm^3$). These results were confirmed by the analysis of the MRTV at D28 (table 13). A massive reduction of the MTV was observed in animals from group 4 (430.89±290.89 $mm^3$) compared to group 1, the vehicle treated animals (1 233.44±663.82 $mm^3$).

The difference between group 1 and the 2 groups treated with the test substance reach the statistical significativity ($p<0.0001$ vs 4−$p=0.003$ vs 3). The difference between group 2 and 4 was also significant ($p=0.001$). In contrast no statistical difference was observed between group 2 (CDDP alone) and group 3 (497c-T2 alone). The first statistical significativity between group 1 and treated group was observed respectively at D22 for groups 3 and D20 for group 4. These results were confirmed by the analysis of the MRTV at D28 (table 13). An important reduction of the MTV was observed in animals from group 4 (430.89±290.89 $mm^3$) compared to group 1, the vehicle treated animals (1 233.44±663.82 $mm^3$).

TABLE 12

Growth inhibition based on T/C ratio

| | T/C ratio (%) Day | | | | | | | |
|---|---|---|---|---|---|---|---|---|
| | D14 | D16 | D18 | D20 | D22 | D24 | D26 | D28 |
| G2 | −70% | 24% | −6% | 17% | 11% | 15% | 45% | 27% |
| G3 | 10% | 33% | 7% | 13% | 26% | 24% | 39% | 27% |
| G4 | 22% | 39% | 8% | 28% | 30% | 41% | 60% | 64% |

The T/C ratio (table 12), which is a parameter of tumor growth inhibition, reveals a slight anti-tumoral activity of the test substance when used as a monotherapy as it reduces by 27% tumor size compared to the vehicle-treated group 1. However, when combined with CDDP, the inhibition rate reach 64% reduction of tumor size relative to the vehicle-treated group 1. These results directly demonstrate that 497C-T2 has a potent anti-tumoral activity when it was used in combination with a cytotoxic agent such as CDDP.

TABLE 13

Mean Relative tumor volume (MRTV) of animals bearing NCI H-460 cells and treated with vehicle (group 1), CDDP alone (Group 2), 497C-T2 (10.0 mg/kg) (Group 3), or combined with 497C-T2 and CDDP (Group 4) according to the scheduled treatment Q2DX8.

MRTV

| Group | D12 | D14 | D16 | D18 | D20 | D22 | D24 | D26 | D28 |
|---|---|---|---|---|---|---|---|---|---|
| 1 | 1 | 1.83 | 3.17 | 2.51 | 3.68 | 4.16 | 5.68 | 7.49 | 8.24 |
| 2 | 1 | 3.11 | 2.39 | 2.66 | 3.08 | 3.70 | 4.84 | 4.11 | 5.98 |
| 3 | 1 | 1.64 | 2.11 | 2.34 | 3.22 | 3.09 | 4.31 | 4.60 | 6.02 |
| 4 | 1 | 1.42 | 1.92 | 2.32 | 2.66 | 2.89 | 3.33 | 2.96 | 2.96 |

As shown in table 13, MRTV reached 2.96 at D28 for the animals of group 4, which confirm the synergistic efficacy of 497C-T2 with Cisplatin. Moreover, cisplatin used alone (group 2) or 497C-T2 used alone (group 3) showed very close MRTV at D28, suggesting that 497C-T2 is also a potent mono-therapy anti-tumor agent.

The invention claimed is:

1. An active polypeptide consisting of:

SEQ ID NO:3; and a means for folding said active polypeptide into an active three dimensional conformation, said means being a sequence comprising 30 to 70 amino acids fused to the C terminus of said active polypeptide, wherein said active polypeptide has anti-angiogenic activity.

2. A medicament comprising the active polypeptide according to claim 1.

3. A pharmaceutical composition comprising the active polypeptide according to claim 1, and one or more pharmaceutically-acceptable excipients.

4. A pharmaceutical composition comprising synergistically effective amounts of the active polypeptide according to claim 1, and a platinum complex selected from the group consisting of cisplatin and carboplatin.

5. A method for inhibiting cancer and/or tumour growth involving angiogenesis comprising administering to a subject in need thereof an effective amount of the active polypeptide of claim 1, a medicament comprising said active polypeptide, or a pharmaceutical composition comprising said active polypeptide in an amount sufficient to inhibit cancer or tumour growth involving angiogenesis.

6. A method for inhibiting cancer or tumour growth involving angiogenesis comprising administering to a subject in need of treatment a synergistic effective amount of the active polypeptide according to claim 1, and a platinum complex selected from the group consisting of cisplatin and carboplatin, which is sufficient to inhibit cancer or tumour growth involving angiogenesis.

* * * * *